(12) United States Patent  (10) Patent No.: US 11,484,732 B2
Liu et al.  (45) Date of Patent: Nov. 1, 2022

(54) MEDICAL RADIATION DEVICE

(71) Applicant: SHANGHAI UNITED IMAGING HEALTHCARE CO., LTD., Shanghai (CN)

(72) Inventors: Jian Liu, Shanghai (CN); Jian Zhang, Shanghai (CN); Yuelin Shao, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 385 days.

(21) Appl. No.: 16/658,009

(22) Filed: Oct. 18, 2019

(65) Prior Publication Data

US 2020/0047002 A1  Feb. 13, 2020

Related U.S. Application Data

(63) Continuation of application No. 15/036,799, filed as application No. PCT/CN2014/091001 on Nov. 13, 2014, now Pat. No. 10,463,882.

(30) Foreign Application Priority Data

Nov. 14, 2013  (CN) .......................... 201320718512.2

(51) Int. Cl.
*A61N 5/10* (2006.01)
*A61B 6/03* (2006.01)
*A61B 6/00* (2006.01)

(52) U.S. Cl.
CPC ............ *A61N 5/1049* (2013.01); *A61B 6/035* (2013.01); *A61B 6/40* (2013.01); *A61N 5/1081* (2013.01);

(Continued)

(58) Field of Classification Search
CPC .......... A61B 6/032; A61B 6/035; A61B 6/00; A61B 6/03; A61B 6/40; A61B 6/447;
(Continued)

(56) References Cited

U.S. PATENT DOCUMENTS 4,658,408 A  4/1987 Amor et al.
5,047,641 A  9/1991 Besseling et al.
(Continued)

FOREIGN PATENT DOCUMENTS

CN  102309824 A  1/2012
CN  102440795 A  5/2012
(Continued)

OTHER PUBLICATIONS

International Search Report in PCT/CN2014/091001 dated Feb. 17, 2015, 2 pages.

*Primary Examiner* — Samuel G Gilbert
(74) *Attorney, Agent, or Firm* — Metis IP LLC

(57)  ABSTRACT

A radiation medical device, including a main support, and a radiation assembly (30) and an imaging assembly (20) respectively located at both ends of the main support. After an imaging scan is completed and pathological tissue positioning pictures are taken, a patient is directly moved to the other end of the main support to allow the radiation assembly (30) to perform radiation therapy to improve the efficiency of the radiation therapy after the completion of pathological tissue positioning, and effectively reduce movement of the patient when the patient is being moved for radiation therapy after the imaging assembly (20) completes pathological tissue positioning, thus reducing pathological tissue positioning error caused by too much movement.

20 Claims, 7 Drawing Sheets

(52) U.S. Cl.
CPC ....... *A61B 6/447* (2013.01); *A61N 2005/1061* (2013.01); *A61N 2005/1063* (2013.01); *A61N 2005/1089* (2013.01)

(58) Field of Classification Search
CPC ................ A61N 5/1049; A61N 5/1081; A61N 2005/1061; A61N 2005/1063; A61N 2005/1089
See application file for complete search history.

(56) References Cited

U.S. PATENT DOCUMENTS

| | | | |
|---|---|---|---|
| 5,175,754 A | 12/1992 | Casey et al. | |
| 5,329,567 A * | 7/1994 | Ikebe | A61B 6/4476 378/20 |
| 6,373,060 B1 | 4/2002 | Yamakawa et al. | |
| 6,385,288 B1 | 5/2002 | Kanematsu | |
| 6,490,476 B1 * | 12/2002 | Townsend | A61B 6/032 250/363.03 |
| 6,842,502 B2 | 1/2005 | Jaffray et al. | |
| 6,914,959 B2 | 7/2005 | Bailey et al. | |
| 7,200,202 B2 | 4/2007 | Kusch et al. | |
| 7,983,380 B2 | 7/2011 | Guertin et al. | |
| 8,218,718 B1 | 7/2012 | Van Herk et al. | |
| 8,989,846 B2 | 3/2015 | Kuduvalli et al. | |
| 9,687,200 B2 | 6/2017 | Maurer, Jr. | |
| 2003/0185338 A1 | 10/2003 | Dafni et al. | |
| 2006/0113482 A1 | 6/2006 | Pelizzari et al. | |
| 2010/0220837 A1 | 9/2010 | Bressel | |
| 2011/0007867 A1 | 1/2011 | Fadler | |
| 2013/0256551 A1 * | 10/2013 | Yao | A61N 5/1082 250/393 |
| 2015/0164441 A1 * | 6/2015 | Niizeki | H05G 1/02 378/11 |

FOREIGN PATENT DOCUMENTS

| | | |
|---|---|---|
| CN | 202489969 U | 10/2012 |
| CN | 203634188 U | 6/2014 |
| DE | 102011081257 A1 | 2/2013 |
| WO | 2014111869 A2 | 7/2014 |

\* cited by examiner

MEDICAL RADIATION DEVICE

CROSS REFERENCE TO RELATED APPLICATION

This application is a continuation of U.S. application Ser. No. 15/036,799, filed on May 14, 2016, which is a U.S. national stage application of International Application No. PCT/CN2014/091001 entitled "Radiation Medical Device," filed on Nov. 13, 2014, designating the United States of America and published in Chinese on May 21, 2015, which in turn claims priority of Chinese Patent Application No. 201320718512.2 entitled "Medical Radiation Device" filed before the State Intellectual Property Office on Nov. 14, 2013, the contents of each of which are hereby incorporated by reference in its entirety.

TECHNICAL FIELD

The present application relates to mechanical field, and more particularly, relates to a radiation medical apparatus.

BACKGROUND

Radiation therapy is a therapeutic method using radiation rays, such as α, β, or γ rays generated by radioactive isotopes, or using X-rays, electron rays, proton rays or other particles generated by various X-ray radiotherapy apparatuses, to impinge diseased tissues of a body. In modern medical therapeutic methods, radiation therapy is widely used in fields such as tumor therapy, etc.

For example, a medical linear accelerator system is a commonly used particle accelerating apparatus for radiation therapy. A medical linear accelerator includes a treatment head in which a radiation source is arranged for irradiating a diseased tissue.

Besides a series of components such as an accelerating tube, an electron gun, movable targets, a magnet-deflection system, a collimator, a flattening filter, etc., the treatment head further includes a high-density shielding layer made of lead for preventing extra radiation rays emitted from the radiation source from irradiating a body during an operation of the linear accelerator, and thus the treatment head has a large mass. The linear accelerator is also provided with counterbalance weights to offset the overturning torque of the treatment head, and thus the volume of an existing linear accelerator is large, which results in troubles for installation, transport, calibration, and maintenance thereof.

Additionally, during a radiation therapy, besides the linear accelerator generating radiation rays, an imaging apparatus, such as a computed tomography (CT) scanner, is also needed to cooperate with the linear accelerator to position the diseased tissue of a body.

Accordingly, during a radiation therapy, the diseased tissue of a patient needs to be positioned via the CT, and then the patient is moved to the linear accelerator to receive the radiation therapy to the diseased tissue, since both the linear accelerator and the CT scanner have large volumes, the distance the patient needs to be moved is large, and the course of the movement is complicated, which easily results in errors in positioning.

Therefore, the problems need to be solved by one person skilled in the art are how to reduce the complexity of a treatment course, to improve the efficacy of a radiation therapy, and to reduce positioning errors during positioning a diseased tissue and irradiating the diseased tissue.

SUMMARY

A medical radiation apparatus is provided by the present disclosure to reduce complexity of a treatment course of a radiation therapy and thus improve the efficacy of the treatment, and to reduce positioning errors during positioning a diseased tissue and performing the radiation treatment on the diseased tissue.

In order to solve the above problems, the medical radiation apparatus provided by the present disclosure includes: a main frame, and a CT assembly and a radiation assembly respectively positioned on an end of the main frame along a first axial direction; the radiation assembly includes a treatment head, rotatable around the first axial direction, for emitting radiation rays; the CT assembly includes a ray tube and a detector that are in an opposing arrangement and respectively positioned on one side of the first axial direction and rotatable around the first axial direction.

Alternatively, the main frame includes a cylindrical body defining openings on both ends thereof, the first axial direction being a central axis of the cylindrical body; the treatment head is fixed onto one end of the cylindrical body, and the CT assembly is positioned on the other end of the cylindrical body.

Alternatively, the ray tube and the detector of the CT assembly are fixed onto an inner wall of the cylindrical body.

Alternatively, the CT assembly includes a CT stator fixed onto the cylindrical body, and a CT rotor mounted on the CT stator; and the CT rotor is rotatable around the first axial direction, and the ray tube and the detector are mounted on the CT rotor.

Alternatively, the CT stator is fixed onto an inner wall of the cylindrical body, and includes a mounting hole defined along the first axial direction; and the CT rotor mounted on the CT stator via a bearing.

Alternatively, the main frame includes a couch plate movable along the first axial direction to pass through the openings on both ends of the cylindrical body; the CT rotor includes a through-hole defined along the first axial direction, and the ray tube and the detector are positioned on the opposite sides of the through-hole, and the couch plate is movable to pass through the through-hole.

Alternatively, the CT stator further includes a CT driving mechanism for driving the CT rotor to rotate; the CT driving mechanism includes a first motor, a first driving wheel coupled to the first motor, and a first driving belt coupled between the CT rotor and the first driving wheel.

Alternatively, the main frame includes a base for supporting the cylindrical body thereon, and the base is provided with a roller driving mechanism for driving the cylindrical body to rotate.

Alternatively, the roller driving mechanism includes a second motor, a second driving wheel coupled to the second motor, and a second driving belt wrapping around the second driving wheel and the surface of the cylindrical body.

Alternatively, the roller driving mechanism further includes a guide wheel arranged on the base.

According to other embodiments of the present disclosure, a medical radiation apparatus provided herein includes: a main frame, rotatable about the central axis thereof; a treatment head, connected with the main frame, for emitting radiation rays; an imaging assembly, defining an imaging through-hole, to image an object located within the imaging through-hole, wherein the imaging assembly is connected with the main frame and rotates along with the main frame.

Alternatively, the main frame includes a cylindrical body substantially coaxial with the imaging through-hole.

Alternatively, the medical radiation apparatus further includes a rotor which the imaging assembly is mounted on, and is connected with the main frame and rotates along with the main frame.

Alternatively, the rotor defines the imaging through-hole, and the main frame includes a cylindrical body substantially coaxial with the imaging through-hole.

Alternatively, the medical radiation apparatus further includes: a stator of the imaging apparatus, connected with the main frame and rotates along with the main frame; and a bearing, connected with the rotor and the stator of the imaging apparatus; wherein the rotor is rotatable via the bearing independent of the stator of the imaging apparatus and the main frame.

Alternatively, the imaging assembly is rotatable around the imaging through-hole independent of the main frame.

Alternatively, the imaging assembly is located within the interior of the main frame.

Alternatively, the imaging assembly is located at least partially within the interior of the main frame.

According to other embodiments of the present disclosure, a medical radiation apparatus provided herein includes: a main frame, rotatable about a central axis thereof; a treatment head, connected with the main frame, for emitting radiation rays; a stator of an imaging apparatus, connected with the main frame and rotates along with the main frame; a rotor, defining an imaging through-hole and equipped with an imaging assembly, wherein the imaging assembly is used to image an object located within the imaging through-hole; and a connecting component, for connecting the stator of the imaging apparatus to the rotor, wherein the rotor is rotatable independent of the stator of the imaging apparatus and the main frame.

Alternatively, the rotor does not rotate along with the main frame.

Alternatively, the connecting component includes a bearing.

Alternatively, the main frame includes a cylindrical body substantially coaxial with the imaging through-hole.

Alternatively, the stator of the imaging apparatus and the rotor are located at least partially within the interior of the main frame.

Alternatively, the stator of the imaging apparatus and the rotor are located completely within the interior of the main frame.

As compared with prior art, the technical solutions of the present disclosure have following advantages:

Positioned at the two ends of the main frame of the medical radiation apparatus are the radiation assembly and the imaging apparatus assembly (for example, a CT assembly), so that a patient can be directly moved to the other end of the main frame to perform radiation treatment by the radiation assembly after the patient is imaged and the diseased tissue is imaged and positioned, thereby improving the efficiency of the procedure of performing radiation therapy after a diseased tissue is positioned, and additionally a positioning error of the diseased tissue caused by excess motion between when the diseased tissue is positioned and when the diseased tissue is subject to radiation treatment can be effectively reduced; moreover, the radiation assembly and the imaging apparatus assembly are respectively arranged on one end of the main frame and can be served as counter balance weights for each other to balance the overturning torque caused by the large masses thereof, which effectively reduces the volume of the medical apparatus, and therefore facilitates installation, transport, calibration, and maintenance of the medical apparatus.

Further, the main frame includes a cylindrical body, and the imaging apparatus assembly and the radiation assembly are positioned on the two ends of the cylindrical body; moreover, the medical radiation apparatus further includes a couch plate capable of passing through the openings defined at both ends of the cylindrical body, so that the patient can be moved to the radiation assembly to receive radiation treatment by directly moving the couch plate after the diseased tissue is positioned. The above technical solutions can avoid a body's motion after the diseased tissue being positioned until the patient being moved to the radiation assembly, and therefore a positioning error of the diseased tissue caused by a body's motion is reduced and accordingly the accuracy of the radiation treatment thereafter is improved.

Further, the medical radiation apparatus includes a stator fixed to the cylindrical body, a rotor mounted on the stator, the rotor is rotatable about a first axial direction, and the ray tube and the detector (together referred to as the imaging assembly) are mounted on the rotor. In the above technical solutions, during the operation of the imaging apparatus assembly, the orientations of the ray tube and the detector for imaging a diseased tissue are adjusted by rotating the rotor; while during the operation of the radiation assembly, the orientation of the treatment head is adjusted by rotating the cylindrical body, i.e. the imaging assembly is rotatable independent of the radiation assembly, thereby reducing the chance that the imaging apparatus assembly and the radiation assembly interfere with each other.

DETAILED DESCRIPTION

As described in the BACKGROUND, existing radiation therapy needs to use an imaging apparatus such as a CT scanner to position the diseased tissue of a patient at first, and then the patient is moved to a linear accelerator to receive a radiation treatment based on an image captured from the imaging apparatus previously in which the diseased tissue is positioned. The course during which the diseased tissue is positioned at first and then the patient is moved to the linear accelerator not only reduces the efficiency of the radiation treatment, but also results in a positioning error of the diseased tissue because the diseased tissue can move due to the motion of the patient's body in the process of moving the patient from the imaging apparatus to the linear accelerator, which brings about difficulties for radiation treatment.

Additionally, because many components in a radiation apparatus used in a radiation treatment, such as a medical linear accelerator, have large masses which produce an overturning torque, the radiation therapy apparatus is further provided with counter balance weights so as to improve the balance of the radiation therapy apparatus. However, it cause difficulty in installation, transport, calibration, and maintenance to the medical radiation apparatus.

Therefore, the present disclosure provides a medical radiation apparatus, which includes an imaging assembly and a radiation assembly, and during a radiation treatment, the patient can be directly moved to the radiation assembly by moving a couch plate to receive a radiation treatment after the patient has been imaged and positioned in the imaging assembly. Thus, the chance of a poisoning error of the diseased tissue caused by the motion of the patient is reduced, and the treatment efficiency is improved. Additionally, the imaging assembly and the radiation assembly can constitute counter balance weights for each other so that the overall volume and weight of the medical radiation apparatus are reduced, thereby reducing the difficulty in installation, transport, calibration, and maintenance to the medical radiation apparatus.

Next, take a CT assembly as an example of the imaging assembly, the technical solutions of the present disclosure is clearly and fully described with reference to the drawings.

FIGS. 1-7 are structural schematic views of the medical radiation apparatus under different states according to some embodiments of the present disclosure.

Figure 1:
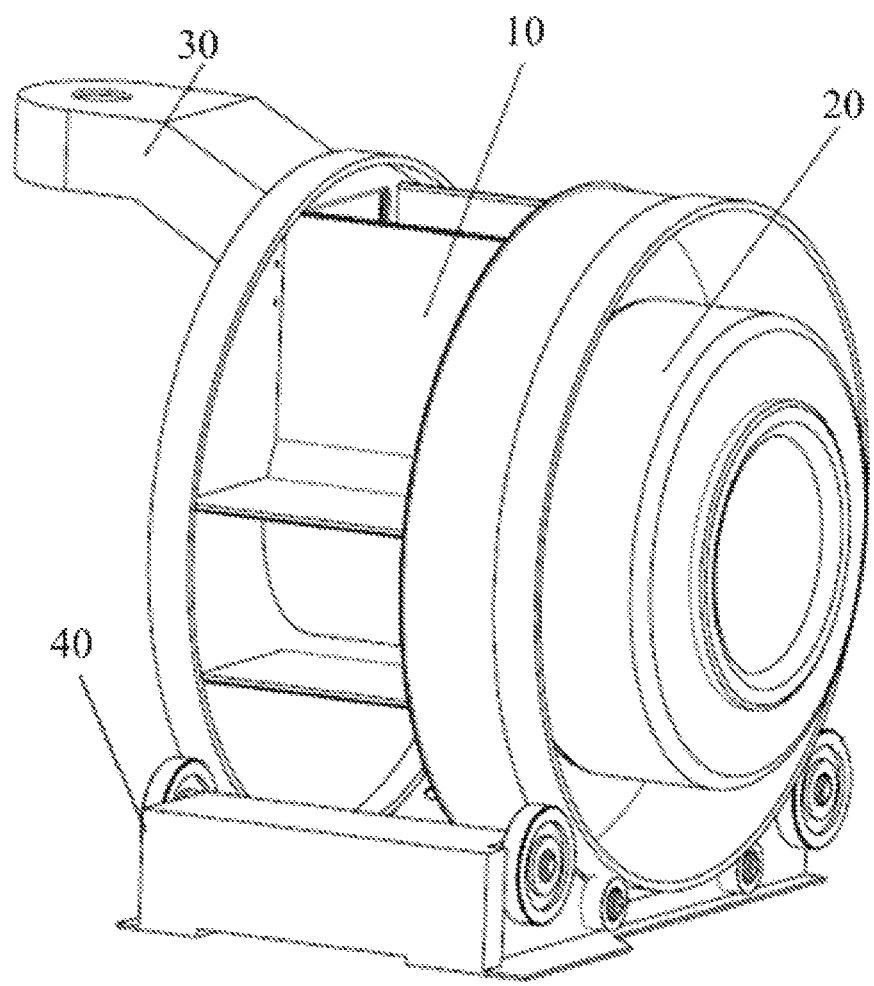
FIG. 1 is a schematic view of the structure of a medical radiation apparatus according to some embodiments of the present disclosure.

Referring to FIG. 1, the medical radiation apparatus provided by the present embodiment includes a main frame, and a CT assembly 20 and a radiation assembly 30 both mounted on the main frame.

Specifically, the main frame includes a cylindrical body 10, the central axis of the cylindrical body 10 indicates a first axial direction. The CT assembly 20 and the radiation assembly 30 are respectively positioned on an end of the cylindrical body 10 along the first axial direction. The CT assembly 20 and the radiation assembly 30 are served as counter balance weights for each other, which improves the overall balance of the medical radiation apparatus.

Figure 2:
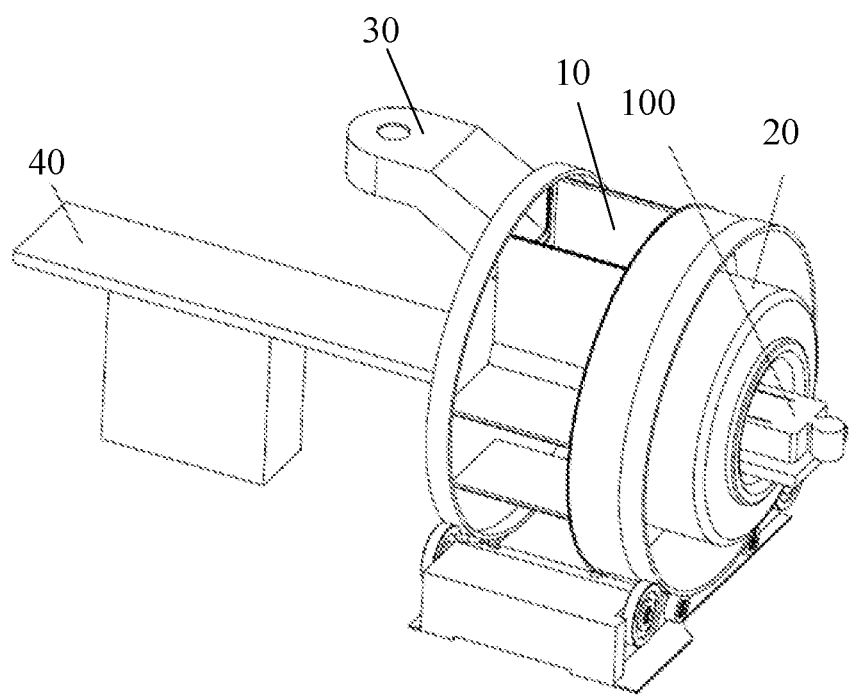
FIGS. 2-3 are schematic views showing an operation of the medical radiation apparatus according to some embodiments of the present embodiment.
Figure 3:
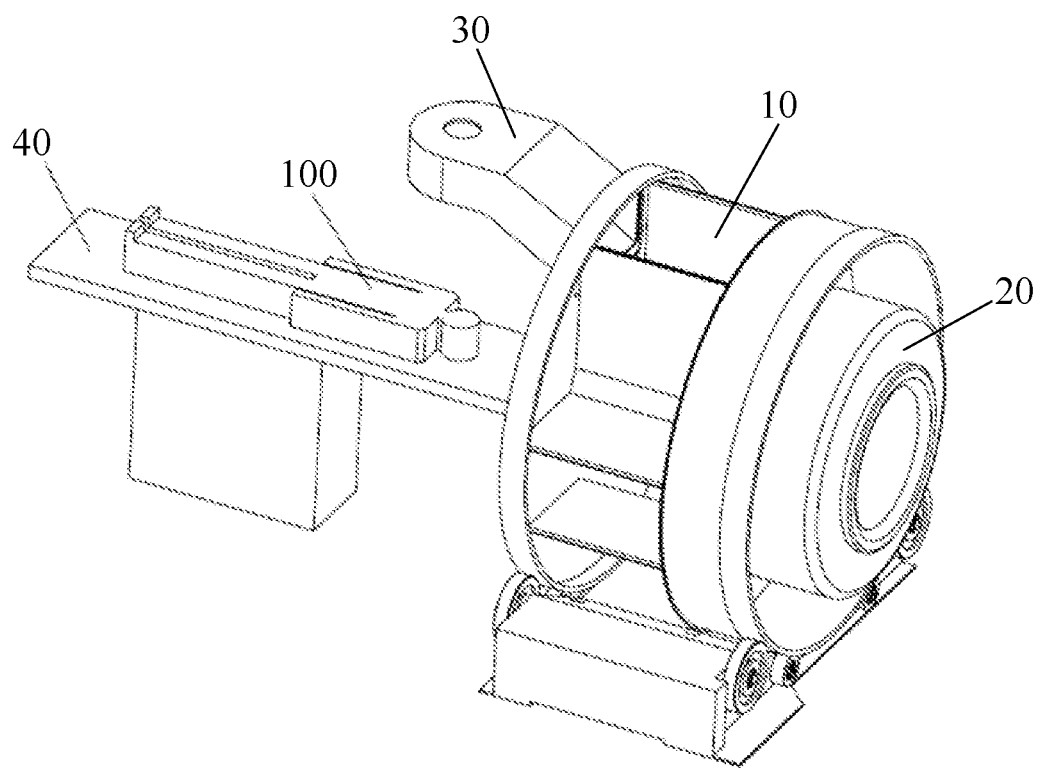

Referring to FIGS. 2 and 3, in the present embodiments, the cylindrical body 10 is a structure with openings defined in both ends, and the medical radiation apparatus further includes a movable couch plate 200. The movable couch plate 200 can move axially along the central axis of the cylindrical body 10, and can pass through the openings at both ends of the cylindrical body 10.

During an operation, as shown in FIG. 2, a patient 100 lies on the movable couch plate 200, and is moved from the opening in the cylindrical body 10 to the end of the CT assembly 20 to receive a CT scan, so as to acquire positioning images of the diseased tissue; then, as shown in FIG. 3, under the condition of keeping the body of the patient 100 unmoved, the movable couch plate 200 is moved to the radiation assembly 30 to where a radiation treatment is performed based on the acquired positioning images of the diseased tissue from the CT assembly 20.

Continuing to refer to FIGS. 1-3, in the embodiments, the radiation assembly includes a treatment head that is used for emitting radiation rays. The treatment head includes a series of components such as an accelerating tube, an electron gun, movable targets, a magnet-deflection system, a collimator, a flattening filter, a shielding layer, etc., which are not repeated here.

The treatment head can axially rotate around the central axis of the cylindrical body 10, and radiation rays from the treatment head are toward the interior of the cylindrical body 10. When an adjustment is performed in a radiation treatment, the treatment head can rotate around the patient so that the orientation of the radiation rays is adjusted.

In the present embodiments, the treatment head is fixed on the cylindrical body 10. The cylindrical body 10 is axially rotatable to drive the treatment head to axially rotate around the central axis of the cylindrical body 10.

Continuing to refer to FIG. 1, the medical radiation apparatus provided by the present embodiments further includes a base 40 for supporting the cylindrical body 10 thereon, and a roller driving mechanism arranged on the base 40 for driving the cylindrical body 10 to axially rotate around the central axis thereof.

Figure 4:
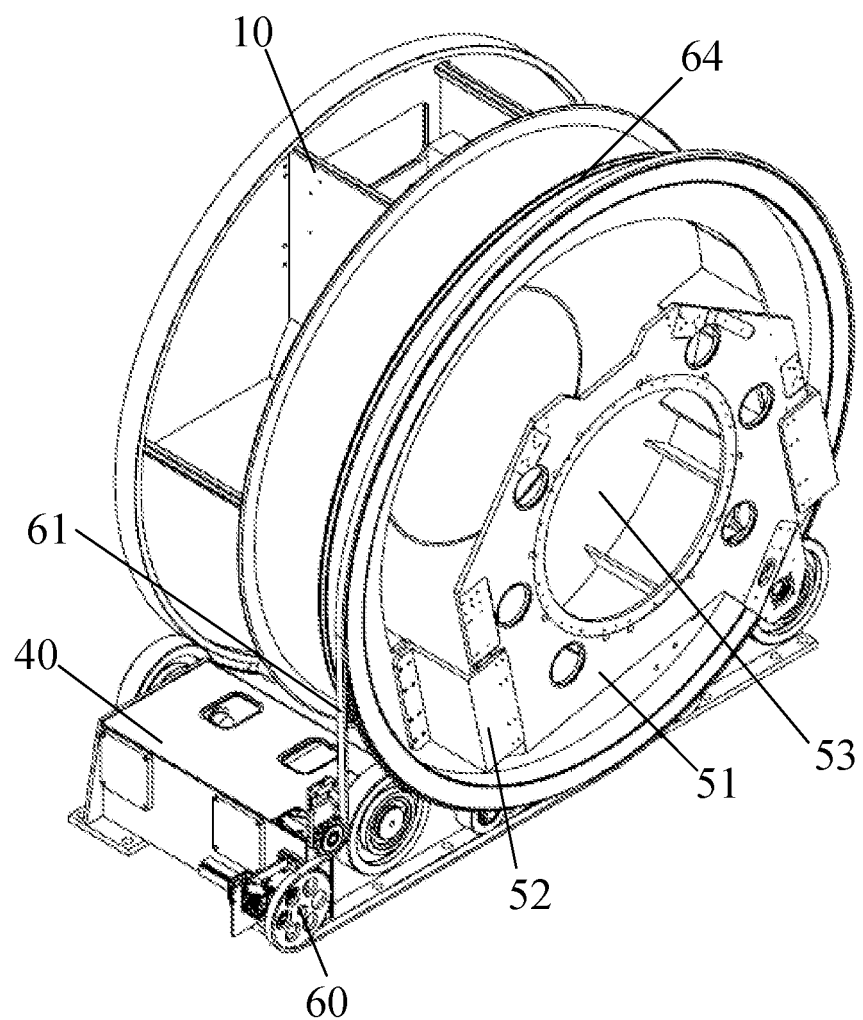
FIG. 4 is a schematic view of a three-dimensional (3D) structure of the interior of the medical radiation apparatus according to some embodiments of the present disclosure.
Figure 5:
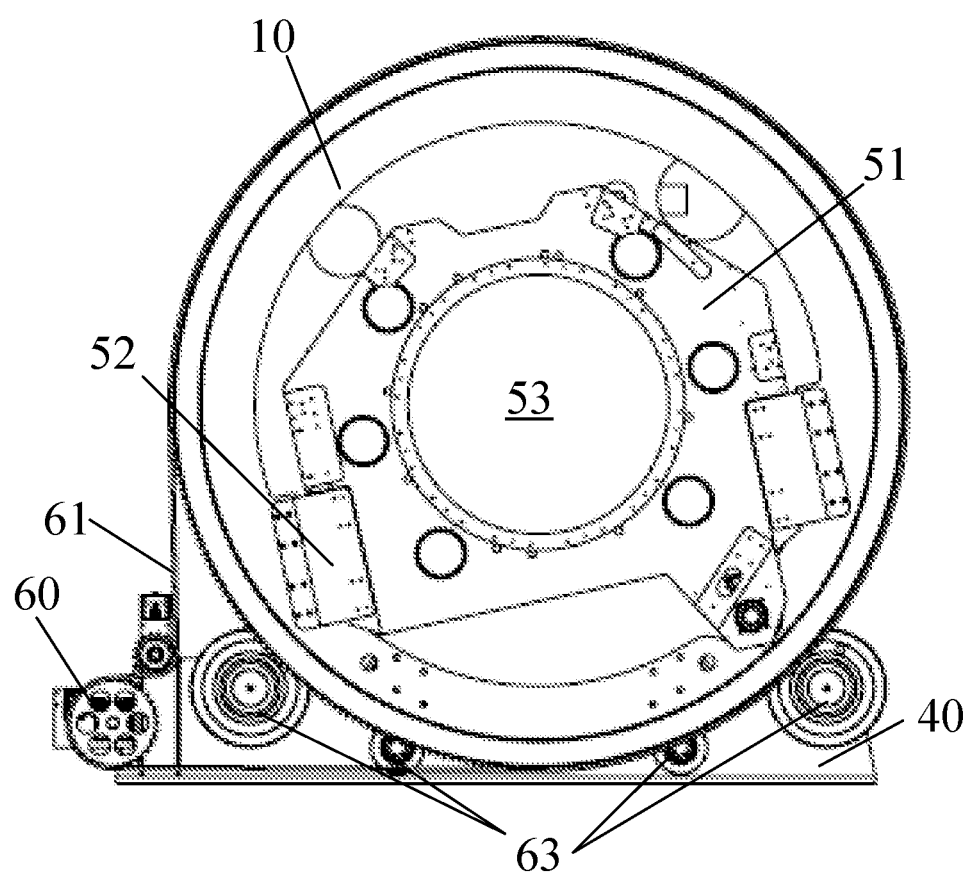
FIG. 5 is a side view of the medical radiation apparatus in FIG. 4.

Specifically, referring to FIG. 4 and FIG. 5, the roller driving mechanism includes a second motor (not shown in the figure), a second driving wheel 60 coupled to the second motor, and a second driving belt 61 wrapping around the second driving wheel 60 and the surface of the cylindrical body 10. In particular, a driving belt groove 64 is defined on the surface of the cylindrical body 10 around the central axis thereof, and the second driving belt 61 is engaged in the driving belt groove 64.

Further, referring to FIGS. 4 and 5, a plurality of guide wheels 63 with a same size or different sizes are mounted on the base 40, the surfaces of the guide wheels 63 press against the surface of the cylindrical body 10, thereby reducing the friction the cylindrical body 10 is subject to during the rotation of the cylindrical body 10 and improving the rotation efficiency of the cylindrical body 10.

In the present embodiments, the CT assembly includes a ray tube and a detector that are respectively positioned on the opposite sides of the central axis of the cylindrical body 10 and opposing to each other. As shown in FIG. 2, during a CT scan is performed to the patient 100, the ray tube and the detector (not shown in FIG. 1) can rotate around the patient 100 so as to adjust the imaging angle of the ray tube and the detector of the CT assembly. One skilled in the art would readily understand that, the above-mentioned ray tube and detector can be jointly referred to as an imaging assembly. Further, the medical radiation apparatus further includes a rotor for mounting the imaging assembly, and the rotor is connected to the main frame so as to rotate along with the main frame as the main frame rotates. An imaging through-hole is defined in the rotor and substantially coaxial with the cylindrical body 10. The imaging assembly can be located completely or at least partially within the interior of the main frame.

Figure 6:
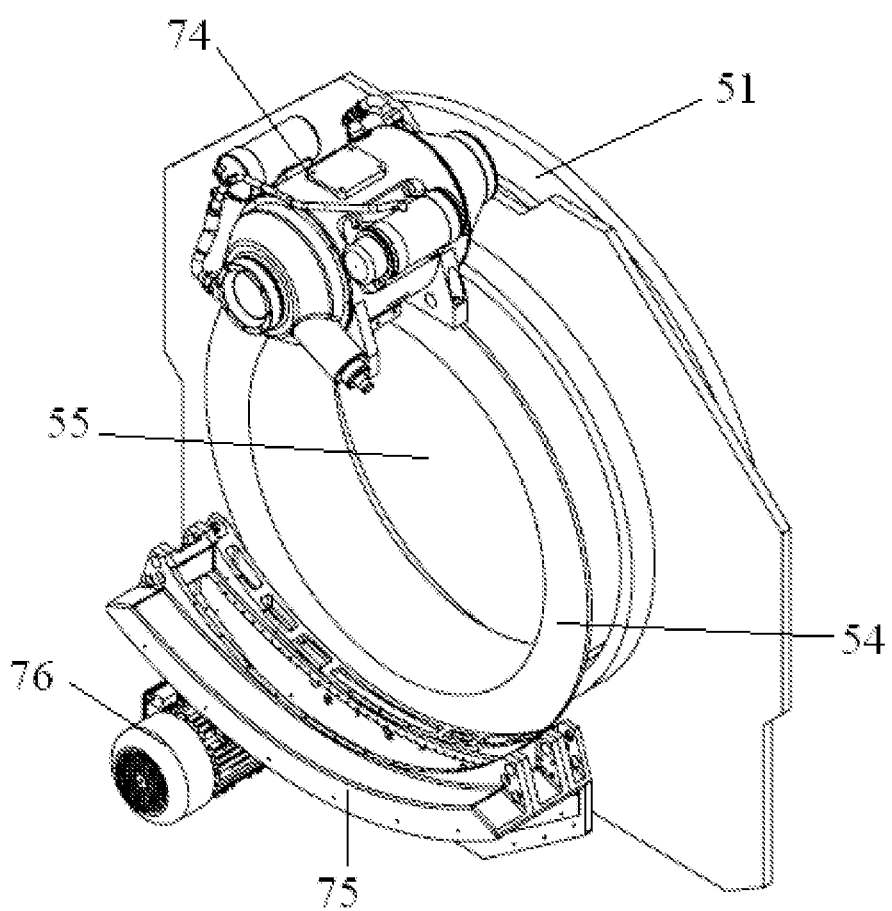
FIG. 6 is a 3D perspective view of the CT assembly in FIG. 1.
Figure 7:
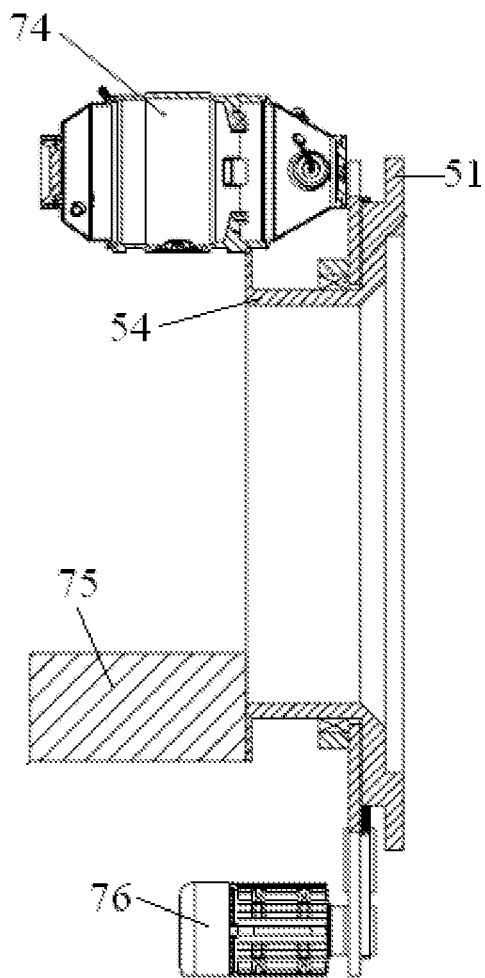
FIG. 7 is a side view of the CT assembly in FIG. 6.

Specifically, referring to FIGS. 5, 6 and 7, in the present embodiments, the CT assembly includes a CT stator 51 and a CT rotor 54. The CT stator 51 is fixed to the inner wall of the cylindrical body 10 via a connecting plate 52, and thus the CT stator 51 can rotate along with the cylindrical body 10. The CT stator 51 has a through-hole 53 defined along the central axis of the cylindrical body 10. As shown in FIG. 7, the CT stator 51 is connected with the rotor 54 via a connecting component such as a bearing 23, and the rotor 54 is rotatable via the bearing 23 independent of the CT stator 51 and the cylindrical body 10.

The CT rotor 54 is mounted on the CT stator 51, a through-hole 55 coaxial with the through-hole 53 is defined on the CT rotor 54 to allow the object therein to be imaged, and the through-hole is substantially coaxial with the cylindrical body 10. The CT rotor 54 is movably connected to the CT stator 51 via a bearing so that the CT rotor 54 can rotate around the central axis of the cylindrical body 10.

Continuing to refer to FIGS. 6 and 7, the ray tube 74 and the detector 75 constituting the imaging assembly are respectively mounted on the CT rotor 54 on the opposite sides of the through-hole 55. The ray tube 74 and the detector 75 constituting the imaging assembly can rotate around the through-hole 55 independent of the main frame. As shown in FIG. 1, the CT stator 51 and the CT rotor 54 are arranged completely within the interior of the main frame. However, one skilled in the art would readily understand that, the CT stator 51 and the CT rotor 54 also can be arranged partially within the interior of the main frame.

Referring to FIGS. 2 and 3, the movable couch plate 200 can pass through the through-holes 53 and 55 and move the patient 100 to the position between the ray tube 74 and the detector 75, the ray tube 74 and the detector 75 are driven by the CT rotor 54 such that, through an adjustment for a CT scan, the ray tube 74 and the detector 75 are positioned at an angle with respect to the patient.

In the present embodiments, the CT stator 51 of the medical radiation apparatus includes a CT driving mechanism for driving the CT rotor 54 to rotate. The CT driving mechanism includes a first motor 76 coupled to the CT rotor 54 and configured to drive the CT rotor 54 to rotate. The CT driving mechanism can be directly fixed on the main frame, and these simple modifications fall within the protection scope of the present disclosure.

Specifically, for example, the CT driving mechanism can include a first driving wheel (not shown in the figures) fixedly coupled to the first motor 76, and a first driving belt (not shown in the figures) configured to connect the first driving wheel and the CT rotor 54. During an operation, the first motor 76 drives the first driving wheel to rotate, and drives the CT rotor 54 to rotate via the first driving belt.

In the present embodiments, the ray tube 74 and the detector 75 constituting the imaging assembly can rotate around the imaging through-hole 55 independent of the main frame, and specifically, the CT rotor 54 of the CT assembly 20 is driven to rotate by the CT driving mechanism, and then the ray tube 74 and the detector 75 are driven by the CT rotor 54 to axially rotate around the central axis of the cylindrical body 10 so that CT scans from different orientations can be performed to the patient 100 and the positioning images of the diseased tissue are obtained; the cylindrical body 10 is driven by the roller driving mechanism to rotate around the central axis thereof, and the treatment head of the radiation assembly 30 is driven by the cylindrical body 10 to rotate around the central axis of the cylindrical body 10, and therefore a radiation treatment from different orientations can be performed to the patient. That is, the CT assembly 20 and the radiation assembly 30 are operated via two sets of driving mechanisms, so the usage flexibility of the CT assembly 20 and the radiation assembly 30 is improved, and the chance of interference between the CT assembly 20 and the radiation assembly 30 is reduced.

Certainly, in embodiments other than the present embodiment, the ray tube and the detector of the CT assembly can be directly fixed on the inner wall of the cylindrical body 10. In this way, the ray tube and the detector of the CT assembly can be driven by the cylindrical body 10 to rotate about the central axis of the cylindrical body 10, and thus the rotation of the ray tube and the detector about the central axis of the cylindrical body 10 is implemented such that the imaging orientation with respect to a patient can be adjusted in a CT scan. These simple modifications fall within the protection scope of the present disclosure.

According to the above-mentioned embodiments of the present disclosure, the imaging apparatus of the medical radiation apparatus is described by taking the CT imaging apparatus as an example. However, one skilled in the art would readily understand that, other medical imaging equipment, for instance, Magnetic Resonance Image (MRI) System, Positron Emission Computed Tomography (PET), (PET-CT), Single Photon Emission Computed Tomography (SPECT), and the like, can also be applied to the technical solutions disclosed in the present disclosure, and the above inventive object of the present disclosure can be obtained by integrating the main frame thereof with the radiation treatment equipment, which is not repeated here.

Although some preferable embodiments are disclosed as above, it is not intended to limit the technical solutions of the present disclosure. Without departing from the spirit and scope of the technical solutions of the present disclosure, any person skilled in the art can implement any possible changes or modifications to the technical solutions of the present disclosure using the methods and technical contents disclosed above, and thus, any simple changes and equivalent modifications to the above embodiments according to technical essence of the present disclosure which does not depart from the technical solutions of the present disclosure, fall within the protection scope of the technical solutions of the present disclosure.

What is claimed is:

1. A medical radiation apparatus comprising:
   a main frame, rotatable about a central axis thereof, comprising a body defining openings on both ends thereof;
   a treatment head, connected with the main frame and fixed to one end of the body, for emitting radiation rays; and
   an imaging assembly, connected with the main frame and positioned on the other end of the body, for imaging an object,
   wherein during a radiation treatment using the treatment head, at least a first part of the imaging assembly rotates along with the main frame when the main frame rotates, and during imaging of the object using the imaging assembly, at least a second part of the imaging assembly is rotatable independent of the main frame.

2. The medical radiation apparatus of claim 1, wherein at least the first part of the imaging assembly is fixed to the main frame.

3. The medical radiation apparatus of claim 1, wherein the imaging assembly comprises a ray tube and a detector in an opposing arrangement, the ray tube and the detector are respectively positioned on opposite sides of a through-hole of the main frame.

4. The medical radiation apparatus of claim 3, wherein the ray tube and the detector are mounted on the at least the second part of the imaging assembly.

5. The medical radiation apparatus of claim 1, wherein the at least the second part of the imaging assembly rotates around the central axis of the main frame.

6. The medical radiation apparatus of claim 1, wherein the main frame comprises a cylindrical body.

7. The medical radiation apparatus of claim 6, wherein the main frame comprises a couch plate movable along a direction of the central axis to pass through the openings defined on both the ends of the cylindrical body; and
   wherein a through-hole is defined in the at least the second part of the imaging assembly along the direction of the central axis, and a ray tube and a detector are positioned on opposite sides of the through-hole, and the couch plate is movable to pass through the through-hole.

8. The medical radiation apparatus of claim 1, wherein the at least the first part of the imaging assembly comprises a driving mechanism for driving the at least the second part of the imaging assembly to rotate; and wherein the driving mechanism comprises a first motor, a first driving wheel coupled to the first motor, and a first driving belt coupled between the at least the second part of the imaging assembly and the first driving wheel.

9. The medical radiation apparatus of claim 1, wherein the imaging assembly is a Positron Emission Computed Tomography-Computed Tomography (PET-CT) assembly.

10. The medical radiation apparatus of claim 1, wherein the imaging assembly is a Computed Tomography (CT) assembly.

11. A medical radiation apparatus comprising:
a main frame, rotatable about a central axis thereof, comprises a body defining openings on both ends thereof;
a treatment head, connected with the main frame and fixed to one end of the body, for emitting radiation rays; and
a Positron Emission Computed Tomography-Computed Tomography (PET-CT) assembly, connected with the main frame and positioned on the other end of the body, for imaging an object,
wherein during a radiation treatment using the treatment head, at least a first part of the PET-CT assembly rotates along with the main frame when the main frame rotates, and during imaging of the object using the PET-CT assembly, at least a second part of the PET-CT assembly is rotatable independent of the main frame.

12. The medical radiation apparatus of claim 11, wherein the at least the first part of the PET-CT assembly is fixed to the main frame.

13. The medical radiation apparatus of claim 11, wherein the PET-CT assembly comprises a ray tube and a detector in an opposing arrangement, the ray tube and the detector are respectively positioned on opposite sides of a through-hole of the main frame.

14. The medical radiation apparatus of claim 13, wherein the ray tube and the detector are mounted on the at least the second part of the PET-CT assembly.

15. The medical radiation apparatus of claim 11, wherein the at least the second part of the PET-CT assembly rotates around the central axis of the main frame.

16. The medical radiation apparatus of claim 11, wherein the main frame comprises a cylindrical body.

17. The medical radiation apparatus of claim 16, wherein the main frame comprises a couch plate movable along a direction of the central axis to pass through the openings defined on both the ends of the cylindrical body; and
wherein a through-hole is defined in the at least the second part of the PET-CT assembly along the direction of the central axis, and a ray tube and a detector are positioned on opposite sides of the through-hole, and the couch plate is movable to pass through the through-hole.

18. The medical radiation apparatus of claim 11, wherein the at least the first part of the PET-CT assembly comprises a driving mechanism for driving the at least the second part of the PET-CT assembly to rotate; and wherein the driving mechanism comprises a first motor, a first driving wheel coupled to the first motor, and a first driving belt coupled between the at least the second part of the PET-CT assembly and the first driving wheel.

19. A medical radiation apparatus comprising:
a main frame, rotatable about a central axis thereof, wherein the main frame comprises a body defining openings on both ends thereof;
a couch, movable form a first position to a second position along the central axis, for supporting an object;
a treatment head, connected with the main frame, for emitting radiation rays and fixed to one end of the body; and
an imaging assembly, connected with the main frame and positioned on the other end of the body, for imaging the object, wherein
during a radiation treatment using the treatment head, the couch is located at the first position, and
during imaging of the object using the imaging assembly, the couch is located at the second position, at least part of the imaging assembly is rotatable independent of the main frame.

20. The medical radiation apparatus of claim 19, wherein the imaging assembly is a Positron Emission Computed Tomography-Computed Tomography (PET-CT) assembly.

* * * * *